US009250353B2

(12) United States Patent
Mariella, Jr. et al.

(10) Patent No.: US 9,250,353 B2
(45) Date of Patent: Feb. 2, 2016

(54) NUCLEAR RADIATION CLEANUP AND URANIUM PROSPECTING

(71) Applicant: LAWRENCE LIVERMORE NATIONAL SECURITY, LLC, Livermore, CA (US)

(72) Inventors: Raymond P. Mariella, Jr., Danville, CA (US); Yves M. Dardenne, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/589,150

(22) Filed: Jan. 5, 2015

(65) Prior Publication Data

US 2015/0234083 A1    Aug. 20, 2015

Related U.S. Application Data

(60) Provisional application No. 61/924,661, filed on Jan. 7, 2014.

(51) Int. Cl.
| | |
|---|---|
| *G01J 1/42* | (2006.01) |
| *G01V 5/00* | (2006.01) |
| *G01V 5/02* | (2006.01) |
| *G01T 7/02* | (2006.01) |
| *G01N 1/02* | (2006.01) |

(52) U.S. Cl.
CPC ................ *G01V 5/0091* (2013.01); *G01T 7/02* (2013.01); *G01V 5/02* (2013.01); *G01N 2001/021* (2013.01); *G01N 2001/028* (2013.01)

(58) Field of Classification Search
CPC ............................ G01T 7/02; G01N 2001/028
See application file for complete search history.

(56) References Cited

U.S. PATENT DOCUMENTS

| | | | | |
|---|---|---|---|---|
| 4,103,553 | A | * | 8/1978 | De Blasiis et al. .......... 73/864.71 |
| 4,267,445 | A | | 5/1981 | Cabbiness et al. |
| 4,345,912 | A | * | 8/1982 | Bartz ............... 436/26 |
| 8,540,173 | B2 | * | 9/2013 | Ichikawa et al. ................... 241/1 |
| 2004/0232323 | A1 | * | 11/2004 | Bosco et al. .................. 250/253 |
| 2006/0097171 | A1 | | 5/2006 | Balchunas et al. |
| 2009/0073586 | A1 | * | 3/2009 | Fry et al. ....................... 359/839 |

FOREIGN PATENT DOCUMENTS

| | | | |
|---|---|---|---|
| JP | 56163470 A | * | 12/1981 |
| JP | 60063499 A | * | 4/1985 |
| WO | 2014113293 | | 7/2014 |

OTHER PUBLICATIONS

Mariella, Jr., et al., "Laser Comminution of Submerged Samples," J. of Applied Physics, vol. 114, 2013, pp. 014904-1-014904-13.

\* cited by examiner

*Primary Examiner* — Kiho Kim
(74) *Attorney, Agent, or Firm* — Eddie E. Scott

(57) ABSTRACT

Apparatus, systems, and methods for nuclear radiation cleanup and uranium prospecting include the steps of identifying an area; collecting samples; sample preparation; identification, assay, and analysis; and relating the samples to the area.

25 Claims, 9 Drawing Sheets

NUCLEAR RADIATION CLEANUP AND URANIUM PROSPECTING

CROSS-REFERENCE TO RELATED APPLICATIONS

This application claims priority to and benefit under 35 U.S.C. §119(e) of U.S. Provisional Patent Application No. 61/924,661 filed Jan. 7, 2014 entitled "Laser-driven, Spatially-resolved sample Preparation," the content of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present application relates to nuclear radiation and more particularly to nuclear radiation cleanup and uranium prospecting.

2. State of Technology

This section provides background information related to the present disclosure which is not necessarily prior art.

The Report by The American Nuclear Society Special Committee on Fukushima" "FUKUSHIMA DAIICHI: ANS Committee Report, March 2012, Revised June 2012," provides the state of technology information reproduced below.
IV. ACCIDENT CLEANUP
The accident at the Fukushima Daiichi NPS has resulted in significant challenges for accident cleanup and waste management. These issues include processing the large volume of contaminated water, debris, soil, secondary wastes, potentially damaged spent fuel within the reactor SFPs, and damaged fuel and fuel debris within the reactors and primary containment structures. Progress has been made in cooling of the reactors, and all the units have reached ambient pressure and temperature conditions, i.e., cold shutdown. Mid-term to long-term waste management issues will continue to be the major technical issues that must be overcome as recovery actions continue toward an acceptable end state. TEPCO (see [13] for TEPCO information on cleanup status) has established a road map that describes elements of the site cleanup and water management, and it is currently developing more detailed mid-range to long-range plans. There are also waste management challenges associated with treatment of contaminated water and the resulting filter and equipment wastes storage and disposal of secondary wastes, contaminated soils, vegetation, and debris decontamination to allow reinforcement of the weakened structures and installation of cooling and gas management systems installation of new secondary containment structures and material-handling equipment.

The Report by The American Nuclear Society Special Committee: "Fukushima, FUKUSHIMA DAIICHI: ANS Committee. Report, March 2012, Revised June 20" is incorporated herein by this reference.

U.S. Pat. No. 4,267,445 for a uranium prospecting method provides the state of technology information reproduced below.

The present invention involves a procedure for mapping the present position and the migration path of uranium or other radioactive material. The procedure involves obtaining a plurality of field samples from a geometric pattern over the surface of the ground. Specimens of quartz or other material exhibiting the thermoluminescence phenomenon are then isolated from the field samples and a thermoluminescence curve is run for the specimens. The specimens are then irradiated at several known levels of radiation, and additional thermoluminescence curves are obtained at each radiation level. From these curves, the amount of natural radiation received by the specimens is determined by comparison of the thermoluminescence curve of the natural specimens against the plurality of curves obtained after subjecting the specimens to known levels of radiation.

The present rate of radioactivity for the samples is then determined by placing radiation dosimeters either in the field on a pattern comparable to the pattern used to obtain the field samples, or alternatively the dosimeters may be placed in the samples themselves. The thermoluminescence from the dosimeters is then measured to obtain a value for the present radioactivity of the samples.

The total amount of present radioactivity from the samples and the amount of gamma radiation can be determined by using both an unshielded and a shielded dosimeter at each field location or in each field sample. The shielded dosimeter will exclude the alpha and beta radiation while allowing the gamma radiation to be measured.

The above steps provide information for each sample point regarding the total lifetime dose of radiation, the present total rate of activity, and the present rate of gamma activity of each sample. This information makes it possible to correlate present activity with historical activity to determine or direct further prospecting activities.

The journal article, Laser comminution of submerged samples, by R. Mariella, Jr., A. Rubenchik, M. Norton, and G. Donohue in JOURNAL OF APPLIED PHYSICS 114, 014904 (2013) provides the state of technology information reproduced below.
FIG. 1 is a photograph of the experimental apparatus, showing the multi-cm path that the laser pulses must pass through water in order to reach the sample surface. Because we expected debris and rubble to absorb UV light more strongly than near-infrared or visible, and because water is more transparent to the 351-nm light, we used 351-nm laser light, directed onto samples of rock [quartzite, a coarse-grained metamorphic rock derived from sandstone, see FIG. 3, or concrete, see FIGS. 2 and 4, as targets that we submerged within 700 ml of de-ionized water.

The journal article, Laser comminution of submerged samples, by R. Mariella, Jr., A. Rubenchik, M. Norton, and G. Donohue in JOURNAL OF APPLIED PHYSICS 114, 014904 (2013) is incorporated herein by this reference.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The disclosed apparatus, systems, and methods of this application include the basic steps of identifying an area; collecting samples; sample preparation; identification, assay, and analysis; and relating the samples to the area. Various embodiments of the disclosed apparatus, systems, and methods include identifying an area of to be sampled, collecting a first sample from a first location in the area with the first location identified, collecting a second sample from a second location in the area with the second location identified, collecting additional samples from additional locations in the area with the additional locations identified. The samples are prepared and processed for identification, assay, and analysis producing first sample results, second sample results, and additional samples results. The first sample results, the second sample results, and the additional samples results are related to the first location, the second location, and the additional locations. Mapping can be produced from the foregoing steps.

The disclosed apparatus, systems, and methods have use in radioactive decontamination, post-detonation analysis of a nuclear event, and uranium exploration. The disclosed apparatus, systems, and methods enable forensic analysis of a heterogeneous sample to retain information of the heterogeneity, rather than combine all material that is present in a sample into one analysis.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1:
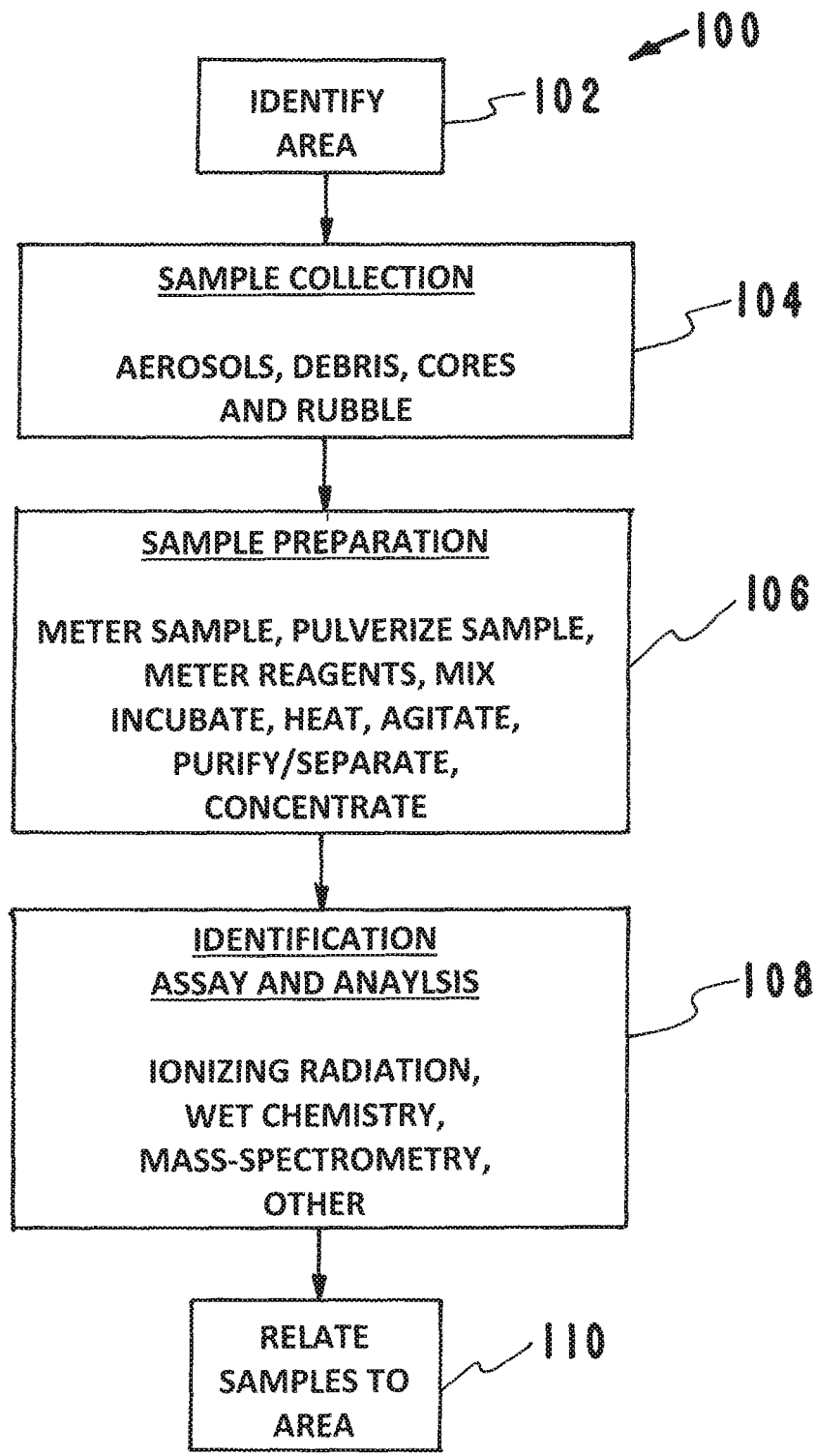
FIG. 1 is a flow chart illustrating the disclosed apparatus, systems, and methods of this application.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Referring now to the drawings and in particular to FIG. 1, a flow chart illustrates the disclosed apparatus, systems, and methods of this application. The apparatus, systems, and methods are designated generally and collectively by the reference numeral 100. The flow chart shows the following basic steps of the disclosed apparatus, systems, and methods 100 of this application:

identify an area—step 102,
sample collection—step 104,
sample preparation—step 106,
identification, assay, and analysis—step 108, and
relate samples to area—step 110.

The basic steps having been identified, additional information will be provided about the individual steps. The "identify an area step 102" includes identifying a nuclear radiation contaminated area from a radiation release from a nuclear power plant accident, identifying a nuclear radiation contaminated area from an explosion of a dirty bomb, identifying a nuclear radiation contaminated area from post detonation of a nuclear weapon, identifying a nuclear radiation contaminated area from other events and purposes. The "identify an area step 102" also includes identifying a uranium prospecting area. The identification of an area step 102 can include using systems for identifying and subsequent mapping the area. For example, the identification of an area step 102 can include using a Global Positioning System (GPS) for identifying the area and individual locations within the area. The GPS information can subsequently be used for mapping the area.

The "sample collection step 104" includes collecting samples if needed for processing elsewhere using aerosols, collecting debris, collecting cores, collecting rubble, and other sample collection systems. Otherwise, the position-tracking system that is employed can simply record the results of chemical analysis for that particular location, if real-time analysis, such as with an inductively-coupled mass spectrometer [ICP-MS], is available. The sample collection step 104 includes manual collection of samples, collection of samples using robots, collection of samples using drones, and other collection of samples techniques. The sample collection step 104 includes retaining the exact location of the sample. For example, the step of retaining the exact location of the sample, if removed, can be accomplished using GPS and other mapping systems. The sample collection step 104 includes collecting samples using aerosols, debris, cores, rubble, etc. The sample collection step 104 includes manual collection of samples, collection of samples using robots, collection of samples using drones, and other collection of samples techniques.

The "sample preparation step 106" could include preparing the sample by coarse breaking or cutting, metering, preparing the sample by metering reagents, preparing the sample by mixing, incubating the sample, preparing the sample using heat, agitating the sample, preparing the sample by purification and separation, concentrating the sample, and other techniques of preparing the sample. The sample preparation step 106 would normally include the laser process we describe that comminutes macroscopic samples into a liquid-based suspension of ultrafine particles [e.g., See FIG. 2 in "Laser comminution of submerged samples," by R. Mariella, Jr., A. Rubenchik, M. Norton, and G. Donohue in JOURNAL OF APPLIED PHYSICS 114, 014904 (2013), above].

The "identification, assay, and analysis step 108" includes identification by ionizing radiation, identification by wet chemistry, identification by mass-spectrometry, and other techniques of identification. The identification, assay, and analysis step 108 can include identification by X-Ray Florescence (XRF) and other identification techniques.

The "relate samples to area step 110" includes using systems for identifying and mapping the area. For example, the relate samples to area step can include using a Global Positioning System (GPS) for identifying the area and individual locations within the area. The GPS information can subsequently be used for mapping the area.

The apparatus, systems, and methods 100 can be a system for nuclear radiation cleanup including identifying an area of to be sampled, collecting a first sample from a first location in the area with the first location identified, collecting a second sample from a second location in the area with the second location identified, collecting additional samples from additional locations in the area with the additional locations identified, analyzing the first sample, the second sample, and the additional samples and producing first sample results, second sample results, and additional samples results. The first sample results, the second sample results, and the additional samples results can be related to the first location, the second location, and the additional locations for nuclear radiation cleanup or uranium prospecting.

The disclosed apparatus, systems, and methods have use in radioactive decontamination, post-detonation analysis of a nuclear event, and uranium exploration. The disclosed apparatus, systems, and methods enable forensic analysis of a heterogeneous sample to retain information of the heterogeneity, rather than combine all material that is present in a sample into one analysis.

The disclosed apparatus, systems, and methods are further described and illustrated by a number of specific examples. Various changes and modifications of these examples will be apparent to those skilled in the art from the description of the examples and by practice of the apparatus, systems, and methods.

Figure 2:
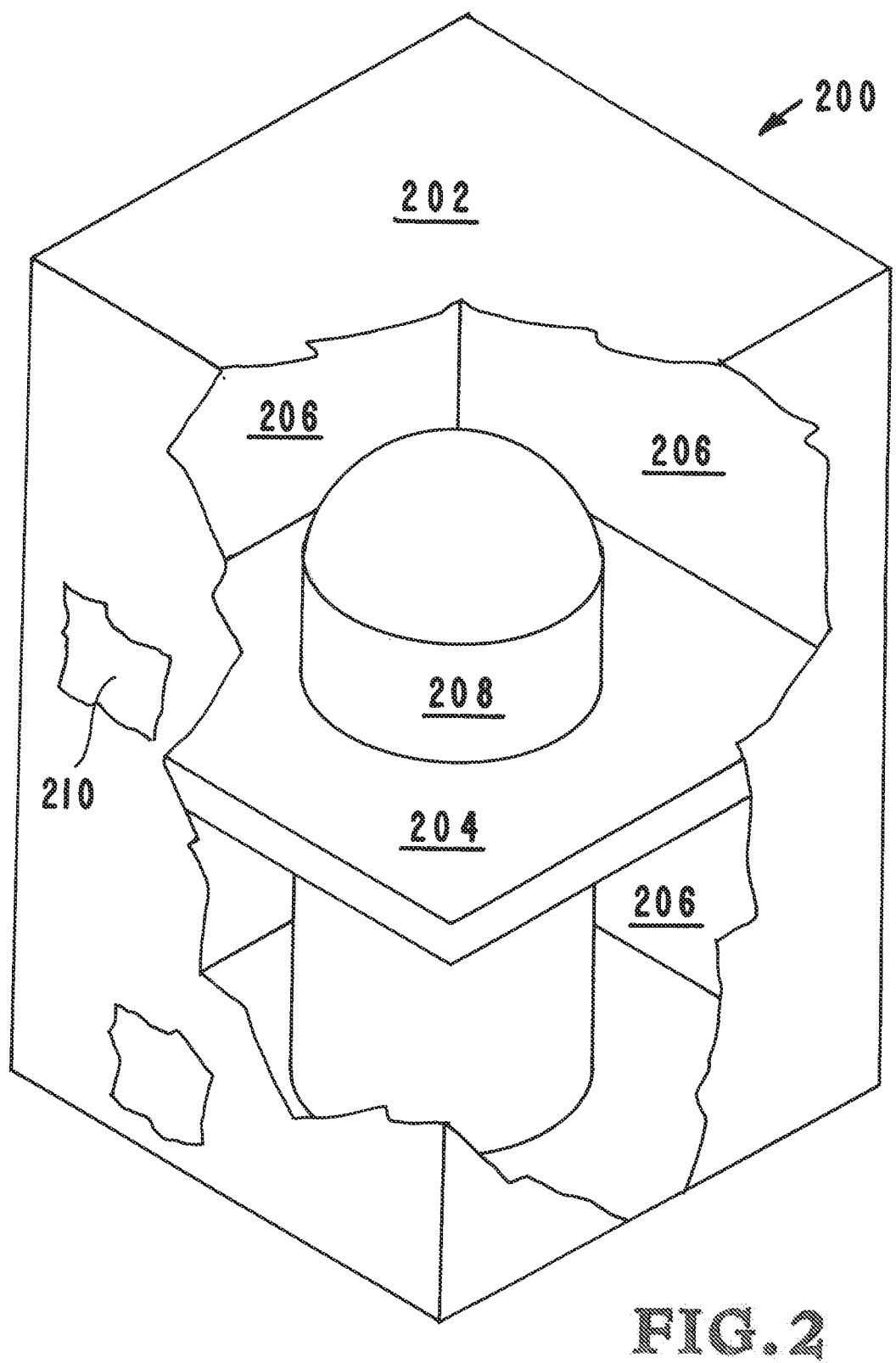
FIG. 2 is an illustration of a damaged nuclear power plant.

Referring now to FIG. 2, a damaged nuclear power plant is illustrated. The damaged nuclear power plant is designated generally by the reference numeral 200. The reactor building 202 includes floors 204, walls 206, and a reactor vessel 208. There are many ways a nuclear power plant can be damaged. A nuclear power plant generates electricity by heating fluid via a nuclear reaction to run a generator. If the heat from that reaction is not removed adequately, the fuel assemblies in the reactor core can melt. A core damage incident can occur even after a reactor is shut down because the fuel continues to produce decay heat. A core damage accident is caused by the loss of sufficient cooling for the nuclear fuel within the reactor core. The reason may be one of several factors, including a loss-of-pressure-control accident, a loss-of-coolant accident (LOCA), an uncontrolled power excursion or, in reactors without a pressure vessel, a fire within the reactor core. Failures in control systems may cause a series of events resulting in loss of cooling. The containment building is the last of several safeguards that prevent the release of radioactivity to the environment. Many commercial reactors are contained within a 1.2-to-2.4-meter (3.9 to 7.9 ft) thick pre-stressed, steel-reinforced, air-tight concrete structures.

In order to access the inside of the damaged reactor building 202, an opening 210 in a wall 206 of the building 202 has been made. In order to avoid sending humans into the building 202 when the building 202 has extremely high radiation levels, a robot is used to help locate, identify, evaluate, analyze, and map radiation levels and damage to the nuclear power plant 200.

Figure 3:
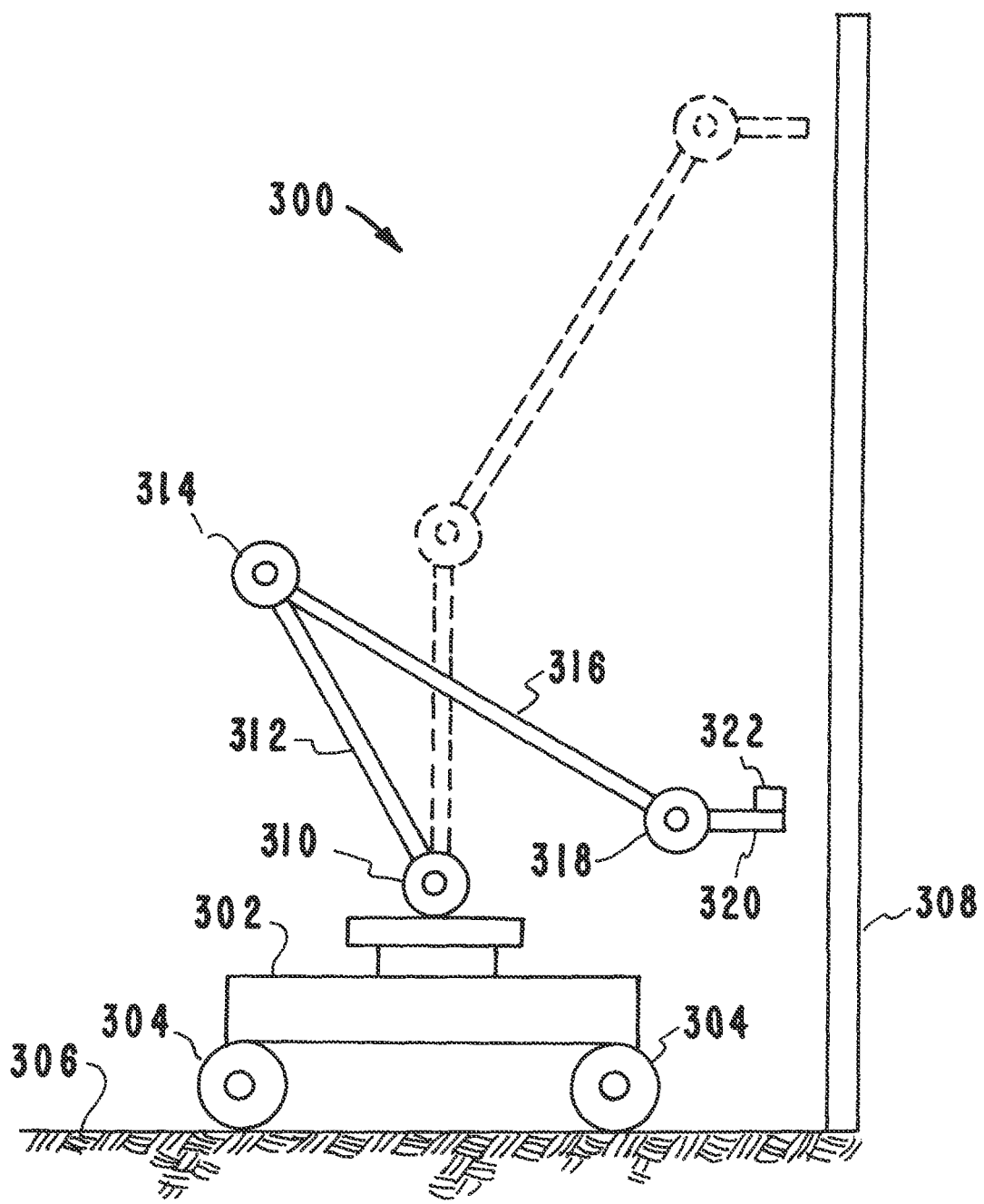
FIG. 3 is an illustration of a robot that can be used to help locate, identify, evaluate, analyze, and map radiation levels and damage to a nuclear power plant.

Referring now to FIG. 3, a robot that can be used to help locate, identify, evaluate, analyze, and map radiation levels and damage to the nuclear power plant. The robot is designated generally by the reference numeral 300. The robot 300 includes a carriage 302 with wheels or treads 304. The robot 300 has articulated arms 312 and 316 mounted on swivels 310, 314, and 318. A unit 320 that can locate, identify, evaluate, analyze, and map radiation levels and damage to the nuclear power plant is mounted on the articulated arm 316. A tracking device 322 is mounted on the unit 320 for tracking movement of the unit 320. The tracking device 322 can be an accelerometer, a GPS device, or other tracking device. The articulated arms and swivels of robot 300 allow the unit 320 to be positioned at locations on the wall 308 and floor 306 of the damaged nuclear power plant.

The unit 320 that can locate, identify, evaluate, analyze, and map radiation levels and damage to the nuclear power plant includes a laser to generate sample particles and a collection system. The laser generates sample particles at a series of locations along the wall of the damaged nuclear power plant. The samples can be stored on board the robot 300 and assigned a discrete address. After the robot 300 has collected samples from an area the robot 300 can return to a base where analysis of the samples can be performed and a map of the surveyed area can be created. In alternative embodiments the laser generates sample particles at a series of locations along the wall of the damaged nuclear power plant and an analysis device that is part of the unit 320 immediately analyzes the particles. Information produced by the analysis is relayed to a central location and a map of the surveyed area can be created.

Figure 4A:
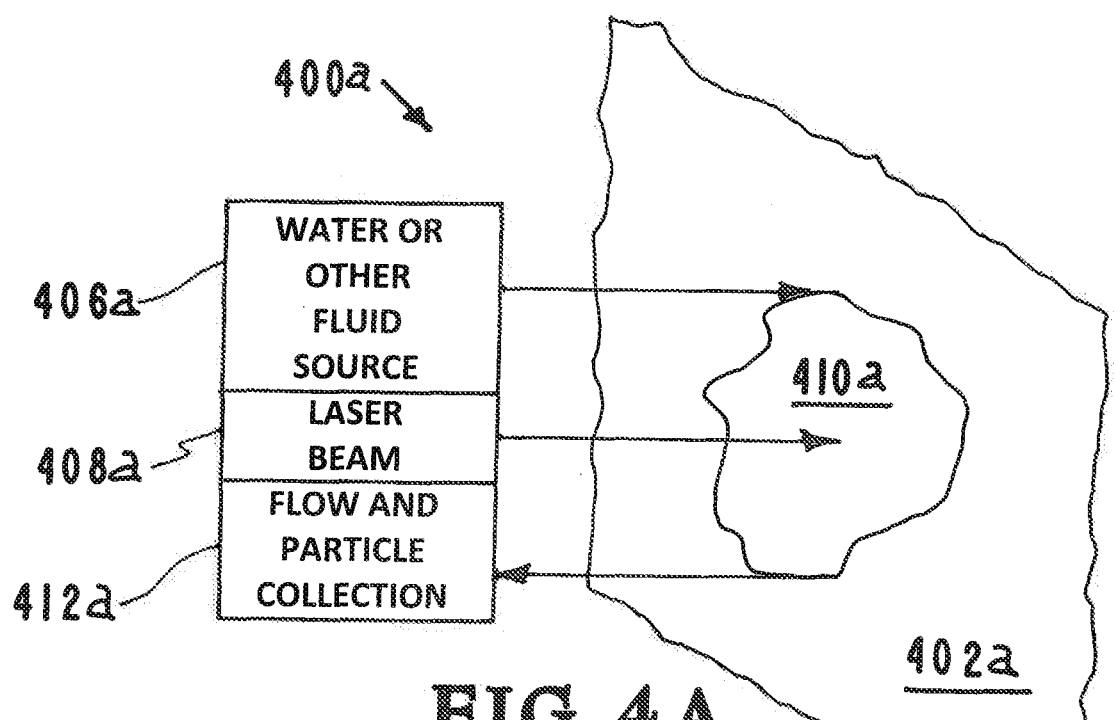
FIGS. 4A and 4B are illustrations of multiple embodiments of a unit that can locate, identify, evaluate, analyze, and map radiation levels and damage to a nuclear power plant.
Figure 4B:
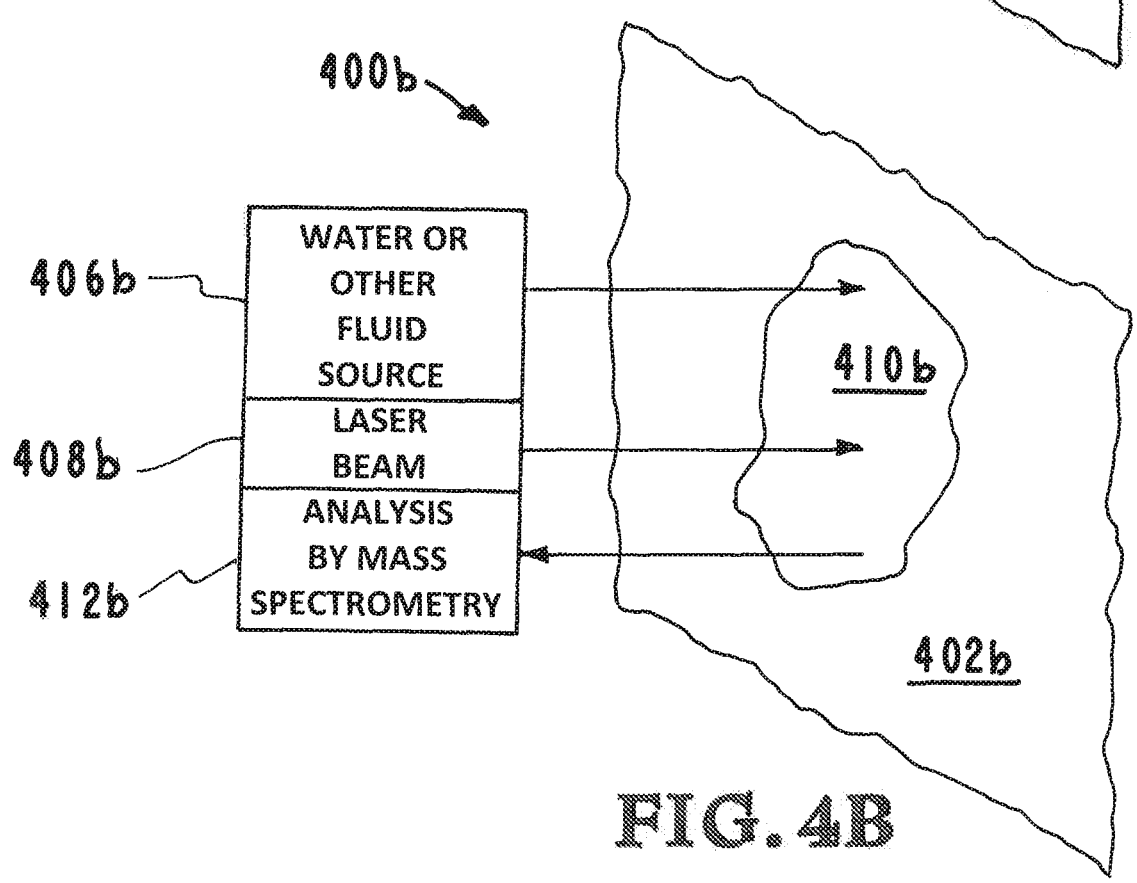

Referring now to FIGS. 4A and 4B, multiple embodiments of a unit that can locate, identify, evaluate, analyze, and map radiation levels and damage to a nuclear power plant are illustrated. The unit 400*a* is shown in FIG. 4A and the unit 400*b* is shown in FIG. 4A.

The units 400*a* and 400*b* can locate, identify, evaluate, analyze, and map radiation levels and damage to the nuclear power plant. The units 400*a* and 400*b* include a laser to generate sample particles and a collection and/or analysis system. The laser generates sample particles at a series of locations along the wall, floor, or other structure in the damaged nuclear power plant. The samples can be stored on board the robot and assigned a discrete address. After the robot has collected samples from an area the robot can return to a base where analysis of the samples can be performed and a map of the surveyed area can be created. In alternative embodiments the laser generates sample particles at a series of locations in the damaged nuclear power plant and an analysis device immediately analyzes the particles. Information produced by the analysis is relayed to a central location and a map of the surveyed area can be created.

The unit shown in FIG. 4A is designated generally by the reference numeral 400. The unit 400*a* uses water directed to the surface 402a being sampled. The water forms a water sheath 410a. A laser produces a laser beam 408a. A number of different lasers can be used. The laser produces laser light strong enough so that the surface of material being treated is heated rapidly enough that the solid surface expands, due to its thermal coefficient of expansion and it and the adjacent fluid become transiently pressurized so that all or some of the solid surface becomes either transiently or semi-permanently dissolved. Materials that are only transiently dissolved then crystallize as a suspension of ultrafine particles, dispersed in the submerging liquid. [e.g. see FIG. 2 of Mariella, et al.] An example of a laser that can be used is a laser based on a Nd:glass zig-zag slab amplifier, with fundamental output at 1053 nm, capable, with a frequency doubler, of emitting 527-nm light or, with a frequency tripler, 351-nm light, or, with a frequency quadrupler, 263-nm light, whose output is roughly rectangular, 15 mm×17 mm, with a nominally flat intensity profile and pulse duration adjustable between 8 and 20 ns. For some of the experiments, a UV-transmitting lens was used to decrease the spot size on the target surface. Another example of a laser that can be used is a laser is a commercial Excimer laser [Coherent-Lambda Physik LPX300 laser], generating 25-ns light pulses at 248-nm wavelength in a 12×30 mm spot.

The laser beam 408a is directed to the water sheath 410a and the surface 402a being sampled. The water sheath 410a moves in flow direction to a collection device 412a. The interaction of the laser beam with the solid surface 408a removes a thin layer of the surface, releasing dissolved material and suspended sample particles at a series of locations along the wall, floor, or other structure in the damaged nuclear power plant. The sheath fluid, containing this dissolved material and suspended sample particles is collected by the collection device 412a. [Henceforth, when we refer to "suspended particles," we also include any material that the laser process removed from the surface that remains dissolved during subsequent analysis] The samples particles are stored on board the robot and assigned a discrete address. The robot returns to a base where analysis of the sample particles is performed and a map of the surveyed area is created.

The unit shown in FIG. 4B is designated generally by the reference numeral 400b. The unit 400b uses water directed to the surface 402b being sampled. Another embodiment would apply this process to flooded surfaces, which could be underground, in a mine, or in a nuclear reactor, as examples. If the surface of interest were submerged in many meters depth of water, for example, and if the laser beam were unable to pass through all of that thickness of water while retaining sufficient power and fluence for transient dissolution of the surface, the robotic system might need to include dry tubing or fiber optics that finally sent the laser beam through a final window, before the beam finally passed through a smaller thickness of submerging of water or other fluid and striking the surface of the sample of interest. In this embodiment, as in the embodiment that used a sheath fluid, the submerging fluid immediately in contact with the laser-illuminated surface needs to be collected.

In the embodiment that treats dry surfaces, the water forms a water sheath 410b. A laser produces a laser beam 408b. The laser beam 408b is directed to the water sheath 410b and the surface 402b being sampled. The water sheath 410b moves in flow direction to a collection and analysis device 412b. The laser beam 408b generates sample particles at a series of locations along the wall, floor, or other structure in the damaged nuclear power plant. The sample particles are received by an analysis device 412b that immediately analyzes the particles. Information produced by the analysis is relayed to a central location and a map of the surveyed area can be created. The analysis device 412b can be a mass spectrometer that in real time analyzes the sample particles and provides sample information that is relayed to a central location where a map of the surveyed area is created.

Figure 5:
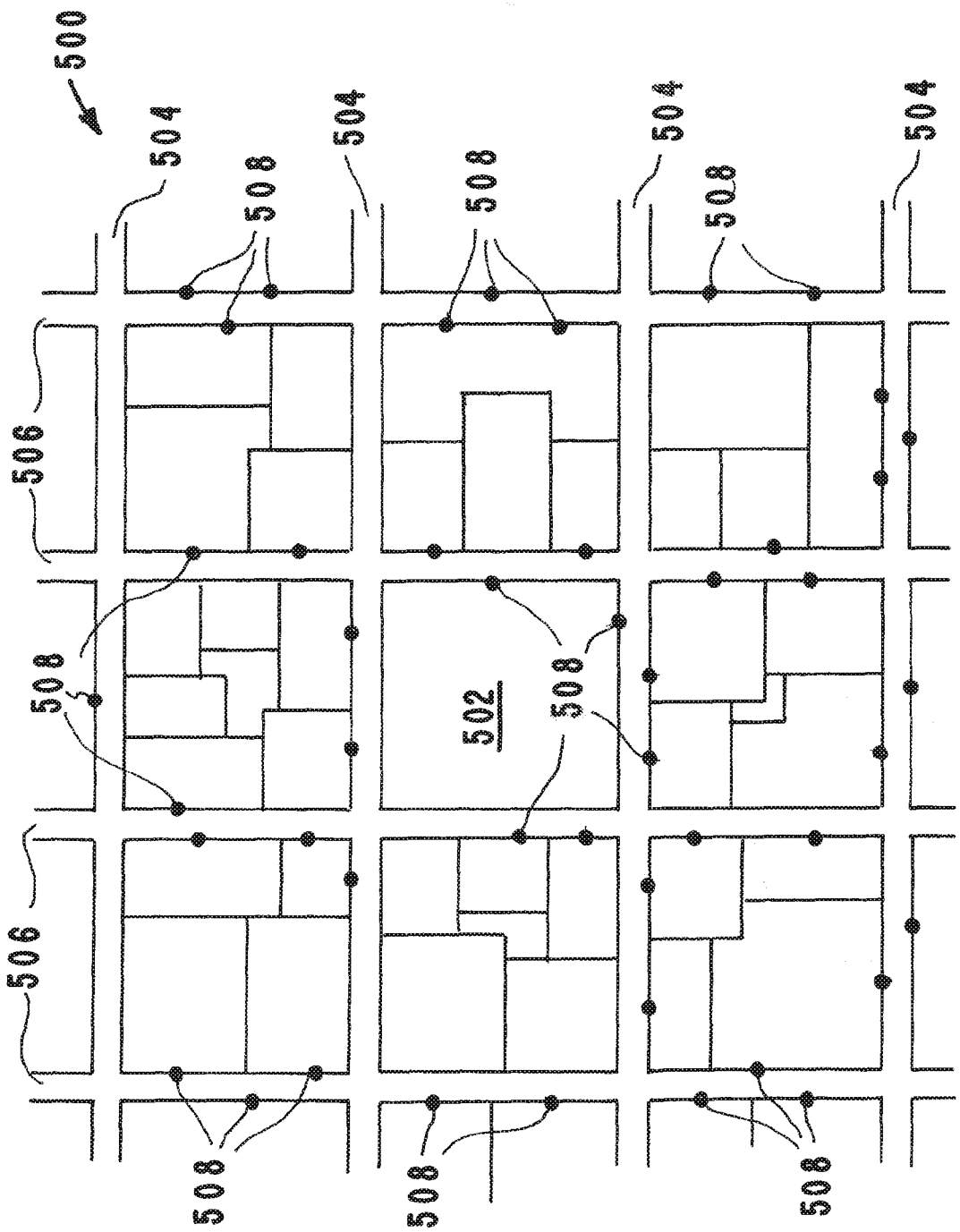
FIG. 5 is an illustration of a contaminated area after detonation of a "dirty bomb."

Referring now to FIG. 5, a contaminated area after detonation of a "dirty bomb" is illustrated. The contaminated area is designated generally by the reference numeral 500. The most commonly discussed type is a so-called dirty bomb, which would use conventional explosives to spread radioactive material. The wide availability of radioactive sources in industrial, commercial, medical, and research uses, combined with clear evidence of terrorist interest in acquiring such material, has led many experts to conclude that a dirty bomb attack in coming years is highly probable A statistical sampling plan needs to be prepared and carried out to determine the distribution and concentration of the deposited radionuclides and to ensure that cleanup of this fallout is done properly. Factors to be considered as part of the statistical sampling plan include: sample acquisition and analysis, grid system configuration and alignment and sample size requirements. Following the initial monitoring assessment to define the extent of contamination there will be a need to estimate in more detail the spatial distribution (pattern) and the total amount of radioactivity present over the region to assess the situation and plan for possible remedial actions. For these purposes, it is usually best if the data are collected on a centrally aligned grid system to ensure that all areas of the region are represented.

As illustrated in FIG. 5, the contaminated area after detonation of a "dirty bomb" includes parallel horizontal streets 504 and parallel vertical streets 506. The ground zero or blast zone where the dirty bomb has been detonated is identified by the reference numeral 502. The locations where samples are taken are identified by the reference numeral 508.

Figure 6:
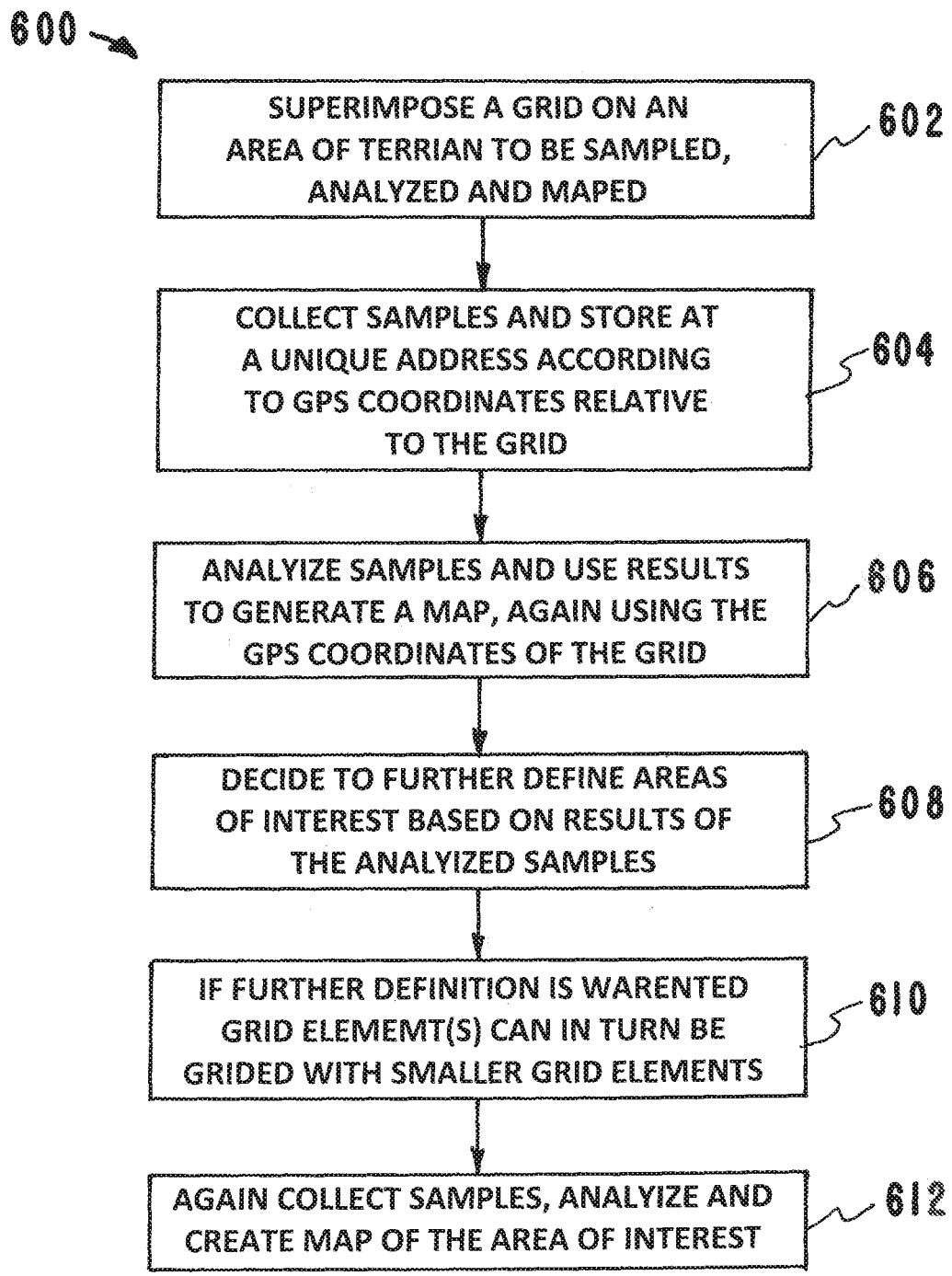
FIG. 6 is a flow chart illustrating apparatus, systems, and methods for cleanup of a contaminated area after detonation of a dirty bomb.

Referring now to FIG. 6, a flow chart illustrates apparatus, systems, and methods for cleanup of a contaminated area after detonation of a dirty bomb. The apparatus, systems, and methods are designated generally and collectively by the reference numeral 600. The flow chart shows the following basic steps of the disclosed apparatus, systems, and methods 600 for cleanup of a contaminated area after detonation of a dirty bomb:

step 602 "superimpose a grid on an area of terrain to be sampled, analyzed and mapped,"

step 604 "collect samples and store at a unique address according to the GPS coordinates relative to the grid,"

step 606 "analyze samples and use results to generate map again using the GPS coordinates of the grid,"

step 608 "decide to further define areas of interest based on results of the analyzed samples,"

step 610 "if further definition is warranted grid element(s) can in turn be gridded with smaller grid elements," and step 612 "again collect samples, analyze and create map of the area of interest."

Figure 7:
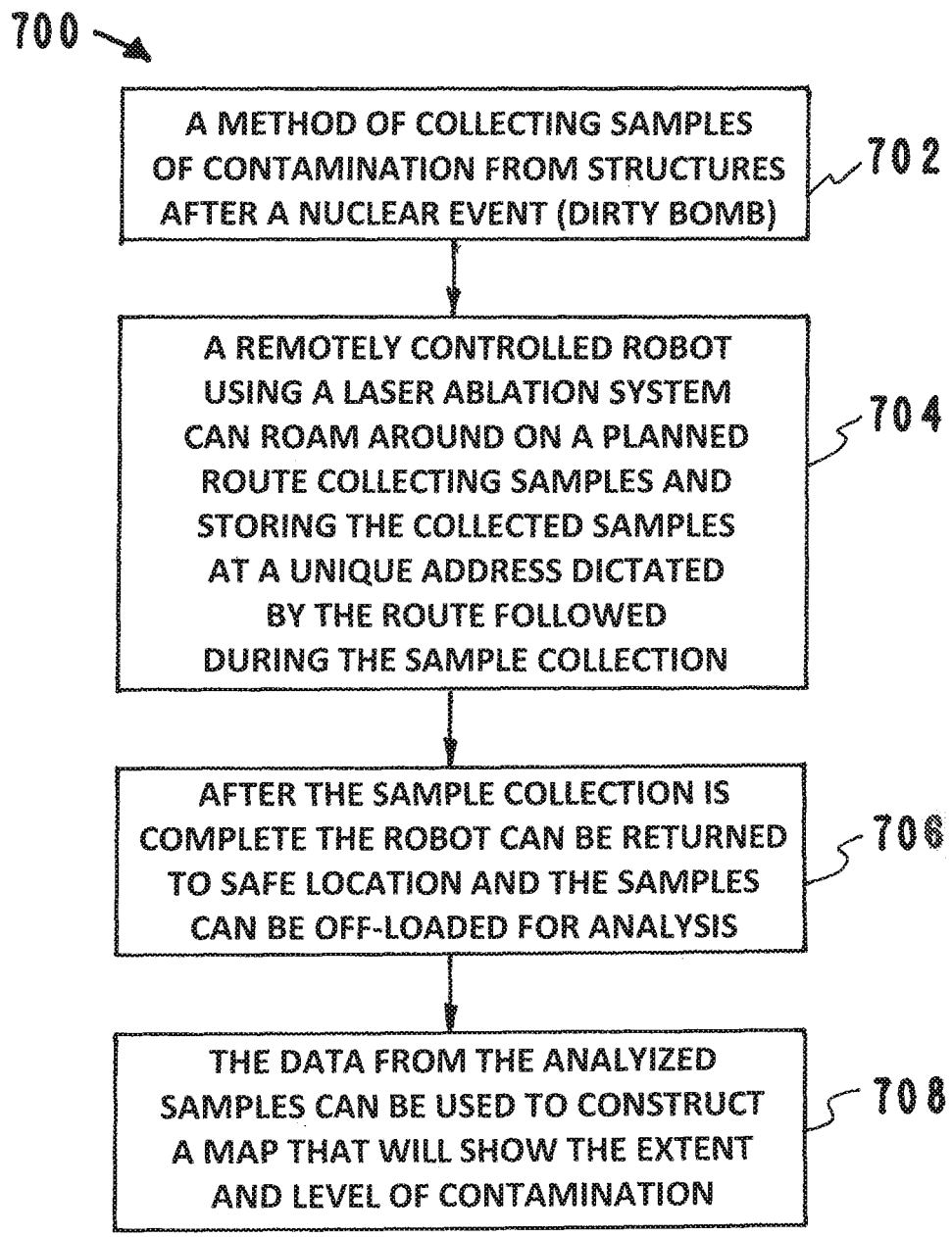
FIG. 7 is a flow chart that provides additional information about the apparatus, systems, and methods for cleanup of a contaminated area after detonation of a dirty bomb shown in FIGS. 5 and 6.

Referring now to FIG. 7, a flow chart provides additional information about the apparatus, systems, and methods for cleanup of a contaminated area after detonation of a dirty bomb shown in FIGS. 5 and 6. The FIG. 7 flow chart is designated generally by the reference numeral 700. The flow chart 700 shows the following basic steps for cleanup of a contaminated area after detonation of a dirty bomb:

step 702 "collection of samples of contamination from structures after a nuclear event (Dirty Bomb),"

step 704 "a remotely controlled robot using a laser processing system can roam around on a planned route collecting samples and string them at a unique address dictated by the route followed during the sample collection,"

step 706 "after the sample collection is compete the robot can be returned to a save location and the samples can be off-loaded for analysis," and step 712 "the data from the analyzed sample can be used to construct a map that will show the extent and level of contamination."

The basic steps having been identified, additional information will be provided about individual steps. The step 702, "collection of samples of contamination from structures after a nuclear event (Dirty Bomb)," includes a unit having a laser to generate sample particles and a collection and/or analysis system. The unit uses water directed to the surface being sampled. The water forms a water sheath. A laser produces laser light strong enough for the fluid and structure to become heated and, concomitantly, transiently heat and pressurize the adjacent fluid so that it has increased dissolving power. The laser beam is directed to the water sheath and the surface being sampled. The water sheath moves in flow direction to a collection device. The laser beam generates sample particles at a series of locations along the wall, floor, or other structure in the contaminated area. The sample particles are collected by the collection device. The samples particles are stored on board the robot and assigned a discrete address. The robot returns to a base where analysis of the sample particles is performed and a map of the surveyed area is created.

The step 704, "remotely controlled robot using a laser processing system can roam around on a planned route collecting samples and string them at a unique address dictated by the route followed during the sample collection," includes a robot with a carriage having wheels or treads. The robot has articulated arms mounted on swivels. A unit that can locate, identify, evaluate, analyze, and map radiation levels in the contaminated area is mounted on the arms. The articulated arms and swivels of the robot allow the unit to be positioned at locations on structures in the contaminated area.

Figure 8:
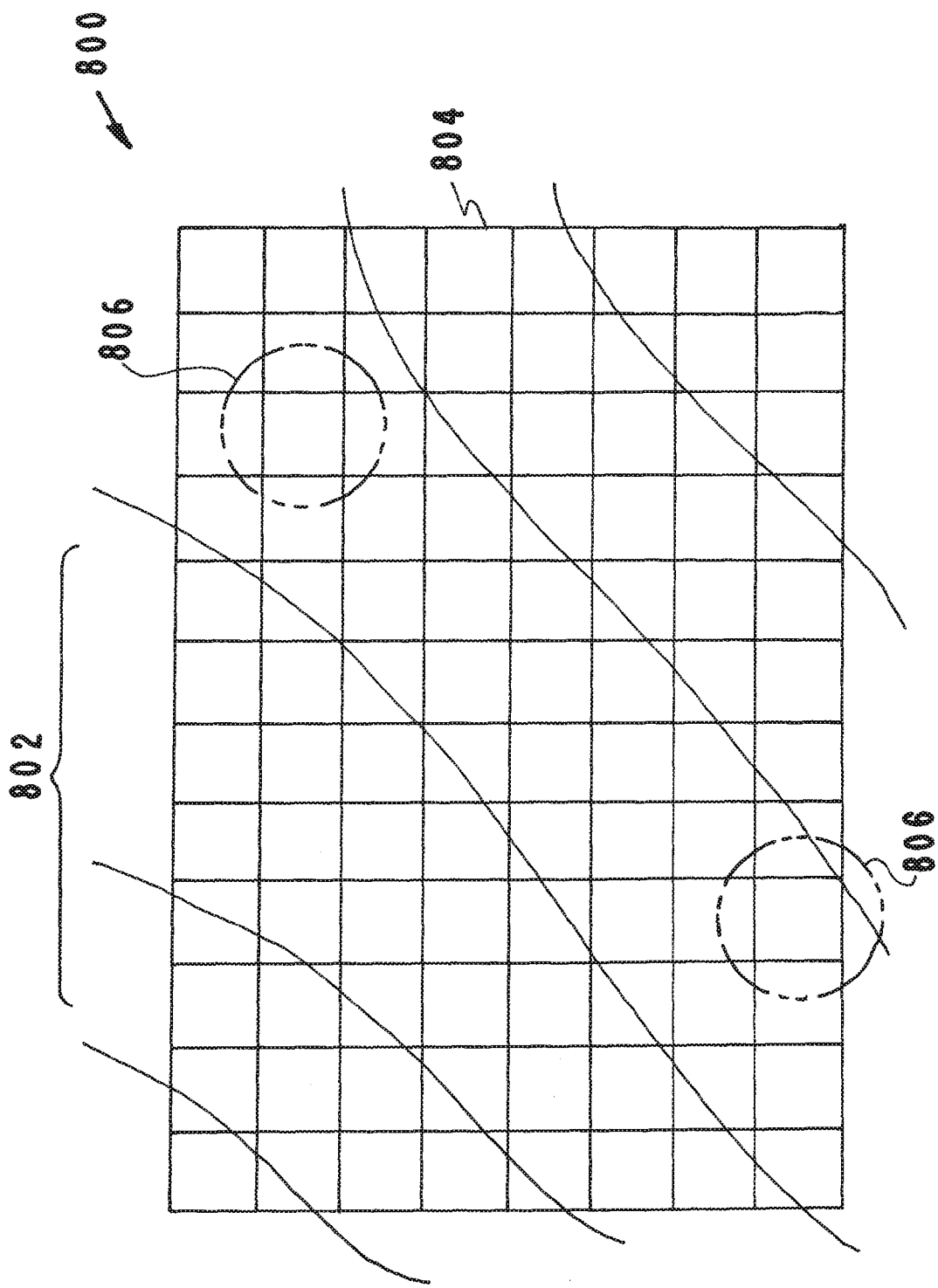
FIG. 8 is an illustration of apparatus, systems, and methods for uranium prospecting.

Referring now to FIG. 8, apparatus, systems, and methods for uranium prospecting are illustrated. Uranium typically occurs in highest concentrations in the mineral uraninite, which is also called pitchblende because of its black color. In a natural, unrefined state, uranium usually exists chemically bound to oxygen as Triuranium octoxide ($U_3O_8$), the most stable, and least chemically reactive form of uranium oxide.

Uranium prospecting includes ground evaluation and sampling to determine if the amount of uranium present is economic to extract. Concentrations of uranium that are economically viable are considered ore and range from about 1,000 up to 200,000 parts per million uranium. The stage of uranium exploration illustrated in FIG. 8 is ground evaluation and obtaining samples. This is designated generally by the reference numeral 800.

An area of terrain 802 is identified. A grid pattern 804 is established on the area of terrain 802. The establishment of a grid pattern 804 includes superimposes a grid on the area of terrain 802 to be sampled, analyzed and mapped. "Samples are collected and stored at individual unique addresses according to the GPS coordinates relative to the grid 804." The samples are analyzed and results of analysis are used to generate a map using the GPS coordinates of the grid 804. Initial evaluation can identify areas of further interest 806. A decision may be made to further define the additional areas of interest based on results of the analyzed samples. If further exploration is warranted the larger grid elements can in turn be gridded with smaller grid elements. Samples are again collected and analyzed to enhance the map of the area of interest.

The discussion of a drone needs massive changes and we should have a face-to-face meeting on this. Complex topic with many complications Referring now to FIGS. 9A, 9B, and 9C a drone for collecting samples for uranium prospecting is illustrated. The drone is designated generally by the reference numeral 900. The drone 900 can locate and collect samples for identification, evaluation, and mapping uranium deposits of interest.

Figure 9A:
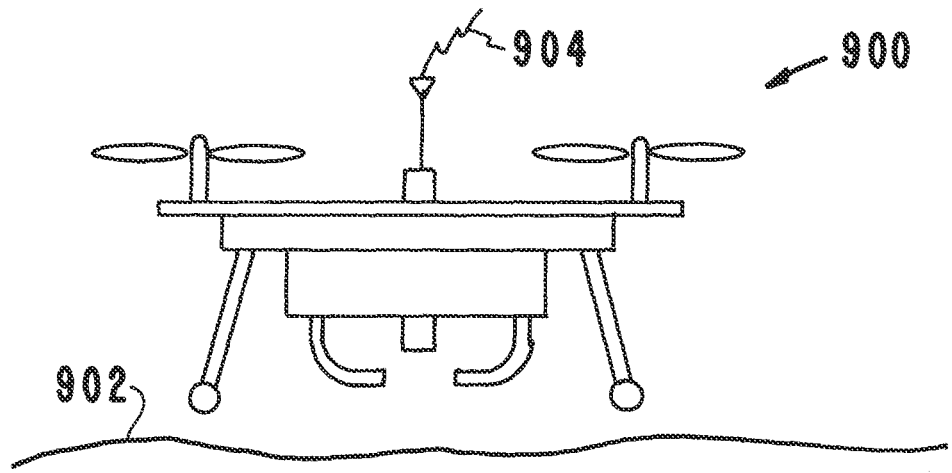
FIGS. 9A, 9B, and 9C illustrate a drone for collecting samples for uranium prospecting.

As illustrated in FIG. 9A the drone 900 contains a GPS system 904 for providing the unique addresses for each sample that is taken in the area of terrain 902.

Figure 9B:
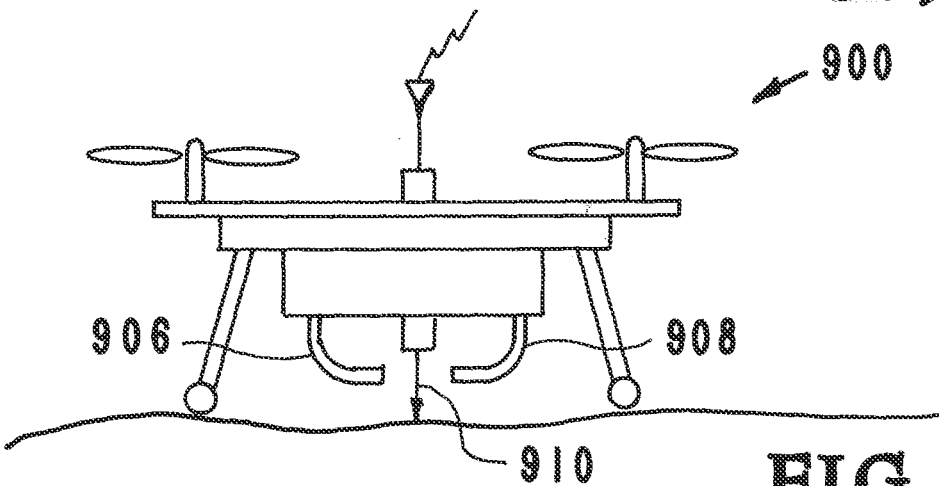

As illustrated in FIG. 9B the drone 900 carries a laser that produces a laser processing beam 910. The interaction of the laser beam 910 with the illuminated surface creates a suspension of ultrafine sample particles at a series of locations within the grid of the terrain 902. The sample particles are collected by the collection device 908. The samples particles are stored on board the drone 900 and assigned a discrete address. The drone 900 returns to a base where analysis of the sample particles is performed and a map of the surveyed uranium prospecting area 902 is created.

Figure 9C:
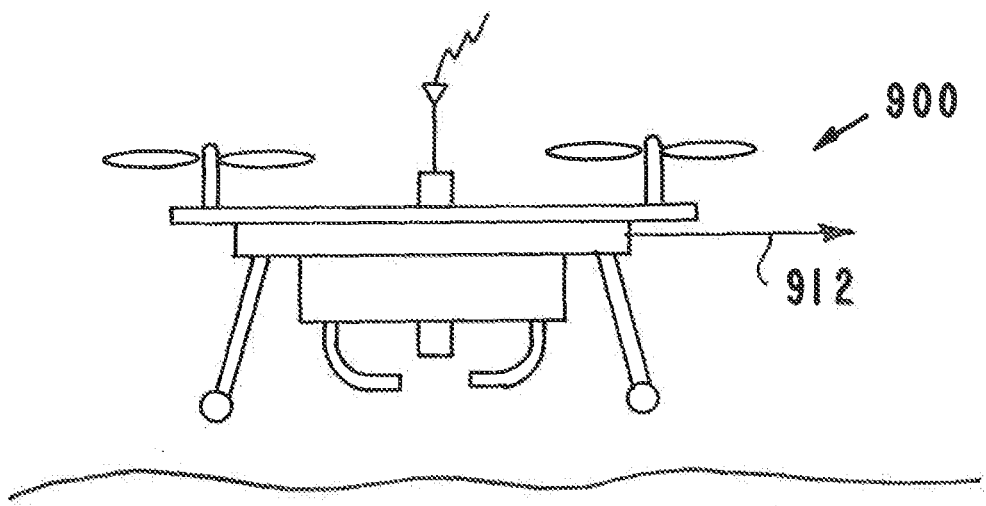

As illustrated in FIG. 9C, after an individual sample is taken the drone 900 moves to the next sampling location. This is illustrated by the arrow 912.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A method of uranium prospecting by sampling solid surfaces, comprising the steps of:
   providing a global positioning system,
   identifying an area of to be sampled using said global positioning system and identifying individual locations within said area to be sampled using said global positioning system wherein the solid surfaces are in said area,
   providing a laser that produces a laser beam,
   collecting samples from the solid surfaces in said area with locations of said samples identified using said laser beam of said laser by directing said laser beam onto the solid surfaces to produce the samples wherein said locations of the samples within said area are retained using said global positioning system that produces retained sample locations,
   analyzing said samples and producing sample results including said retained sample locations, and
   relating said sample results to said locations using said global positioning system and said retained sample locations.

2. The method of uranium prospecting of claim 1 further comprising the step of providing a map of said area using said retained sample locations by relating said retained sample locations to said area using said global positioning system.

3. The method of uranium prospecting of claim 1 wherein said step of collecting samples from the solid surfaces in said area with locations of said samples identified using said laser beam of said laser by directing said laser beam onto the solid surfaces to produce the samples wherein said locations of the samples within said area are retained using said global positioning system that produces retained sample locations includes directing said laser beam onto the solid surface thereby producing particle samples from the solid surface.

4. The method of uranium prospecting of claim 1 wherein said step of collecting samples from the solid surfaces in said area with locations of said samples identified using said laser beam of said laser by directing said laser beam onto the solid surfaces to produce the samples wherein said locations of the samples within said area are retained using said global positioning system that produces retained sample locations includes directing water onto the solid surface and directing said laser beam onto the water and onto the solid surface producing particle samples from the solid surface.

5. The method of uranium prospecting of claim 4 wherein said step of providing a laser that produces a laser beam comprises providing a laser that produces a laser beam that is a pulsed laser beam.

6. The method of radiation cleanup or uranium prospecting of claim 4 wherein said step of collecting samples from the solid surfaces in said area with locations of said samples identified using said laser beam of said laser by directing said laser beam onto the solid surfaces to produce the samples wherein said locations of the samples within said area are retained using said global positioning system that produces retained sample locations includes using a robot for collecting said samples.

7. The method of uranium prospecting of claim 6 wherein said laser is carried by said robot and said laser is used for directing said laser beam onto the solid surface producing particle samples from the solid surface.

8. The method of uranium prospecting of claim 7 wherein said laser beam is a pulsed laser beam.

9. The method of uranium prospecting of claim 1 wherein said step of collecting samples from the solid surfaces in said area with locations of said samples identified using said laser beam of said laser by directing said laser beam onto the solid surfaces to produce the samples wherein said locations of the samples within said area are retained using said global positioning system that produces retained sample locations includes using a drone for collecting samples from the solid surfaces in said area with locations of said samples identified using said laser beam of said laser by directing said laser beam onto the solid surfaces to produce the samples wherein said locations of the samples within said area are retained using said global positioning system that produces retained sample locations.

10. The method of uranium prospecting of claim 9 wherein said laser that produces a laser beam is carried by said drone.

11. The method of uranium prospecting of claim 10 further comprising the step of providing a collection device on said drone and wherein said samples are collected in said collection device.

12. A method of nuclear radiation cleanup including sampling solid surfaces, comprising the steps of:
    providing a global positioning system,
    identifying a radiation contaminated area of to be sampled using said global positioning system and identifying individual locations within said radiation contaminated area of to be sampled using said global positioning system wherein the solid surfaces are in said individual locations in said radiation contaminated area,
    providing a robot,
    providing a laser connected to said robot wherein said laser produces a laser beam,
    collecting samples from the solid surfaces in said individual locations in said radiation contaminated area with said individual locations of said samples identified using said robot, said laser, said laser beam and said global positioning system by directing said laser beam onto the solid surfaces to produce the samples,
    analyzing said samples and producing sample results including said individual locations of said samples, and
    relating said sample results to said locations using said global positioning system.

13. The method of radiation cleanup of claim 12 further comprising providing a map of said radiation contaminated area by relating said individual locations of said samples using said global positioning system.

14. The method of radiation cleanup of claim 12 wherein said step of collecting samples from the solid surfaces in said individual locations in said radiation contaminated area with said individual locations of said samples identified includes directing said laser beam onto the solid surface producing particle samples from the solid surface.

15. The method of radiation cleanup of claim 12 wherein said step of collecting samples from the solid surfaces in said individual locations in said radiation contaminated area with said individual locations of said samples identified includes directing water onto the solid surface and directing said laser beam onto the water and the solid surface producing particle samples from the solid surface.

16. The method of radiation cleanup of claim 15 wherein said step of directing said laser beam onto the water and the solid surface producing particle samples from the solid surface comprises directing a pulsed laser beam onto the water and the solid surface producing particle samples from the solid surface.

17. The method of radiation cleanup of claim 12 wherein the nuclear radiation cleanup is cleanup of a contaminated area after detonation of a dirty bomb further comprising the step of superimposing a grid on the contaminated area and wherein said step of relating said sample results to said locations using said global positioning system comprises relating said sample results to said grid using said global positioning system.

18. The method of radiation cleanup of claim 17 further comprising generating a map of the contaminated area using said sample results related to said grid using said global positioning system.

19. The method of radiation cleanup or uranium prospecting of claim 18 wherein said step of relating said sample results to said grid using said global positioning system comprises providing said sample results with unique addresses using said global positioning system and relating said sample results to said grid using said unique addresses.

20. The method of radiation cleanup of claim 19 wherein said step of generating a map of the contaminated area using said sample results related to said grid using said global positioning system comprises generating a map of the contaminated area using said sample results related to said grid using said unique addresses.

21. The method of radiation cleanup of claim 20 wherein said step of identifying a radiation contaminated area of to be sampled using said global positioning system and identifying individual locations within said radiation contaminated area of to be sampled using said global positioning system comprises using said global positioning system to provide unique addresses of said samples and relating said unique addresses of said samples to identify individual locations within said radiation contaminated area.

22. The method of radiation cleanup claim 20 wherein said step of identifying a radiation contaminated area of to be sampled using said global positioning system and identifying individual locations within said radiation contaminated area of to be sampled using said global positioning system comprises using said global positioning system to provide unique addresses of said samples, relating said unique addresses of said samples to identify individual locations within said radiation contaminated area, and generating a map of the contaminated area using said unique addresses.

23. A method of uranium prospecting, comprising the steps of:
providing a global positioning system,
identifying a uranium prospecting area of to be sampled using said global positioning system and identifying individual locations within said uranium prospecting area to be sampled using said global positioning system wherein said individual locations have material with solid surfaces,
providing a drone,
providing a laser connected to said drone wherein said laser produces a laser beam,
collecting samples in said uranium prospecting area with locations of said samples identified using said laser beam of said laser by directing said laser beam onto said solid surfaces to produce samples wherein said locations of said samples within said individual locations are retained using said global positioning system that produces retained sample locations,
analyzing said samples and producing sample results including said retained sample locations, and
relating said sample results to said locations using said global positioning system and said retained sample locations.

24. The method of radiation cleanup of claim 23 further comprising providing a map of said uranium prospecting area by relating said sample results to said locations using said global positioning system and said retained sample locations.

25. An apparatus for radiation cleanup comprising:
a global positioning system for identifying a radiation cleanup area of to be sampled wherein said radiation cleanup area to be sampled includes material with a solid surface,
a robot adapted to enter said radiation cleanup area,
a laser carried by said robot that produces a laser beam wherein said laser beam is directed to said solid surface of said material and produces particle samples,
a storage unit on said robot for collecting said particle samples in said radiation cleanup area with locations of said particle samples identified using said global positioning system,
an analyzer for analyzing said particle samples and producing sample results including said locations of said particle samples, and
a system for relating said sample results to said locations of said particle samples using said global positioning means.

* * * * *